(12) United States Patent
Chen et al.

(10) Patent No.: US 6,579,901 B2
(45) Date of Patent: Jun. 17, 2003

(54) PHARMACEUTICAL COMPOSITIONS AND METHODS FOR TREATING IMMUNE-RESPONSE ASSOCIATED DISEASES OF THE SURFACE AND THE ANTERIOR SEGMENT OF THE EYE

(76) Inventors: Jiaqi Chen, 54 Xianlienan Road, Guangzhou, Guangdong (CN); Yongmin Liu, 54 Xianlienan Road, Guangzhou, Guangdong (CN)

( * ) Notice: Subject to any disclaimer, the term of this patent is extended or adjusted under 35 U.S.C. 154(b) by 0 days.

(21) Appl. No.: 09/888,342

(22) Filed: Jun. 22, 2001

(65) Prior Publication Data

US 2002/0173516 A1 Nov. 21, 2002

(51) Int. Cl.7 .................................................. A61K 31/35
(52) U.S. Cl. ........................................ 514/455; 514/912
(58) Field of Search .................................. 514/455, 912

(56) References Cited

U.S. PATENT DOCUMENTS 5,540,931 A * 7/1996 Hewitt et al. ............... 424/434

OTHER PUBLICATIONS

Suppression of corneal graft rejection in rabbits by a new immunosuppressive agent, FK506. *Transplant Proc. 1996*, 21(1):3156–3158.

Ocular absorption of topically applied FK506 from liposomal and oil formulations in the rabbit eye. *Invest. Ophthalmol. Vis. Sci..*, 1993, 34:2737–2742.

Use of topical FK506 in a corneal graft rejection model in Lewis rats, *Invest. Ophthalmol. Vis. Sci.*, 1997; 38(5):901–9.

FK–506 delays corneal graft rejection in a model of corneal xenotransplantation. J. Ocul. Pharmacol. Ther., 1996;.12(4):425–31.

Effect of FK 506 administered topically versus intramuscularly on suppression of the corneal immune reaction in rats. Ophthalmologica, 1996; 210(3):175–9.

Effects of topical FK506 on endotoxin–induced uveitis (EIU) in the Lewis rat, *Curr. Eye. Res.*, 1995; 14(3):209–14.

* cited by examiner

*Primary Examiner*—Zohreh Fay
(74) *Attorney, Agent, or Firm*—Crowell & Moring LLP

(57) ABSTRACT

A pharmaceutical composition for the treatment of immune-related diseases of ocular surface and the anterior segment of the eye. More specifically, the invention relates to a composition comprising tacrolimus in a pharmaceutically acceptable formulation, particularly a suitable local treatment formulation, such as eye drops and ointments. Also disclosed is a method for the treatment of immune-response related ocular diseases of the anterior segment of the eye and the eye surface, wherein the method comprises administering to a patient in need thereof the pharmaceutical composition of the present invention. The method of the present invention preferably further comprises administering to the patient an immunosuppressant in addition to tacrolimus.

10 Claims, No Drawings

PHARMACEUTICAL COMPOSITIONS AND METHODS FOR TREATING IMMUNE-RESPONSE ASSOCIATED DISEASES OF THE SURFACE AND THE ANTERIOR SEGMENT OF THE EYE

This application claims priority to Chinese Patent Application No. 00 1 17235.2, filed on Jul. 27, 2000.

BACKGROUND OF THE INVENTION

This invention relates to pharmaceutical compositions and methods for the treatment of diseases associated with immune response in the anterior segment and the surface of the eye.

Diseases associated with immune response in the anterior segment and surface of the eye include erosive corneal ulcer, rejection reactions in cornea transplantation, allergic inflammation of conjunctiva and corneal limbus. At present, the medicines of choice for treatment of these diseases are glucocorticosteroids. These medicines, however, have strong side-effects after long-term topical administration. These side effects include skin atrophy, inhibition of healing of corneal epithelium and lesion, corticosteroid glaucoma, and complicated cataract.

Cyclosporin A (CsA) has been used as alternatives to glucocorticosteroid. Although CsA has good therapeutic effects on immune-response associated ocular surface diseases, recent research showed that CsA has limited local penetration. Consequently, immune inhibition in non-surface ocular tissues is primarily achieved via the systemic pharmacological effect of CsA. In addition, oil-based eye-drops of CsA have significant irritant effect on eyes.

Therefore, there is a need for novel pharmaceutical compositions that do not have the drawbacks of the present therapies.

SUMMARY OF THE INVENTION

The invention relates to a pharmaceutical composition for the treatment of immune-related diseases of ocular surface and the anterior segment of the eye. More specifically, the invention relates to a composition comprising tacrolimus in a pharmaceutically acceptable formulation, particularly a suitable local treatment formulation, such as eye drops, ointments. Also disclosed is a method for the treatment of immune-response related ocular diseases of the of the anterior segment of the eye and the eye surface, wherein the method comprises administering to a patient in need thereof the pharmaceutical composition of the present invention. The method of the present invention preferably further comprises administering to the patient an immunosuppressant in addition to tacrolimus.

DETAILED DESCRIPTION OF THE INVENTION

Tacrolimus is a macrolide immunosuppressant produced by *Streptomyces tsukubaensis*. It suppresses both humoral and cellular immune responses. The drug inhibits a calcium/calmodulin-dependent phosphatase, calcineurin, which prevents the activation of T-cell-specific transcription factors that are involved in lymphokine expression. Other mechanisms are probably also involved in the pharmacologic and toxic effects of tacrolimus. (Schwaninger M et al. *Naunyn Schmiedbergs Arch Pharmacol.* 1993; 348: 541–545.)

Absorption of the drug from the gastrointestinal tract after administration of an oral dose is variable. The absorption half-life as measured in 16 patients is 5.7±4.6 hours. Maximum blood and plasma concentrations are reached 1.5 to 3.5 hours after administration. Disposition of the drug is biphasic. The terminal elimination half-life is 11.7±3.9 hours in transplant patients, compared with 21.2 hours in healthy volunteers.

Tacrolimus has a formula $C_{44}H_{69}NO_{12} \cdot H_2O$, a molecular weight of 822D and its structure is as shown below:

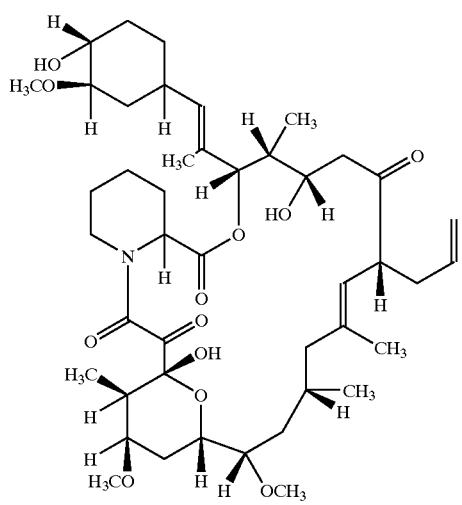

It is a white powder at room temperature, readily dissolved in organic solvents such as methanol, ethanol, and chloroform. It dissolves poorly in water.

Tacrolimus is a member of hydrophobic immunosuppressants in macrolide-type family. The family includes CsA, rapamycin (or sirolimus), and ascomycin. Administration in vitro demonstrates that its effect on immunosuppression is 10–100 folds of that of CsA. Clinically, it has been systemically applied with success to treat rejection in transplantation and autoimmune diseases, and has been routinely used in the transplantation of kidney, liver, and heart. When used systemically, however, tacrolimus has strong side effects similar to that of CsA. In addition, the relatively high dose required by the systemic administration incurs high costs.

As discussed above, presently, locally applied pharmaceutical compositions for the treatment of immune-response related eye diseases, especially those of the anterior or the surface of the eye, have strong, undesirable side effects. Other presently available pharmaceutical compositions rely on systemic administration and also have similar, strong undesirable side effects.

To date there has been no report that tacrolimus may be used for treating diseases associated with immune response in the anterior segment and the surface of the eye.

The inventions disclosed herein overcome the drawbacks of the severe topical side-effects of current therapeutic drugs for immune-response related ocular diseases, particularly the diseases of the anterior segment of the eye and the eye surface. The compositions and methods disclosed herein comprise the use of tacrolimus in a local or topical way. The present compositions and methods have better topical effect, but less toxic and other side effects.

According to the present invention, tacrolimus may be formulated in any pharmaceutical compositions suitable for topical administration, including eye drops, ointments, creams and powders. In a preferred embodiment, anhydrous tacrolimus is used.

In a preferred embodiment, the pharmaceutical composition of the invention is an eye drop. The most preferred composition of the eye drop comprises, in a 100 ml water solution, the following ingredients: 0.02–0.2 grams of tacrolimus; 0–1.5 grams of NaCl, pharmaceutically acceptable amounts of surfactant, and antibiotics or bacterial suppressant (collectively "bacterial suppressant" hereinafter), and a suitable amount of thickener to adjust the viscosity of the composition to 40–50 cP.

Suitable bacterial suppressant for the present invention may be any commonly used, pharmaceutically suitable one, except for phenylmercuric nitrate. Suitable concentrations for the bacterial suppressant can be determined by a skilled person according to routine procedures. For example, (1) thimerosal at a concentration of 0.02–0.04% g/ml; (2) quaternary ammonium salts, including geramine, bromogeramine, domiphen bromide, myristylpicolinin bromide, and chlorhexidine, whose effective concentrations are 0.002–0.01% (g/ml); (3) ethanols, such as trichlorbutanolum at 0.3–0.6% (g/ml); (4) nipagins at concentrations of 0.03–0.06% (g/ml); and (5) acids, such as sorbic acid with a concentration of 0.01–0.08% (g/ml).

A skilled artisan will recognize that any commonly used, pharmaceutically suitable thickener can be used for the present invention. Preferred examples include hydroxypropyl methylcellulose, sodium hyaluronide, polyvinyl alcohol, polyvinyl pyrrolidone. The degree of polymerization may be routinely controlled such that the eye drops achieve a final viscosity of 40–50 cP. It is obvious to those skilled in the art that an increased viscosity reduces eye irritation and prolong the residual time of the eye drops. There are many surfactants frequently used for ophthalmologic purposes and all of them are suitable for this invention. Examples include a polyoxyethylated castor oil (HCO60) with a dosage of 0.8–8.0% g/ml.

In a particularly preferred embodiment, the eye drop of the present invention may be prepared according to the following procedure. The thickener is dispersed in a suitable, small amount of water, and the solutions is cooled. Separately, the surfactant, sodium chloride, and bacterial suppressant are dissolved in water. The two solutions are then combined, mixed and filtered, and the volume is adjusted with water. Finally, tacrolimus is dissolved in the mixed solution and the resultant preparation is filtered and dispersed into individual packages.

According to another preferred embodiment, the pharmaceutical composition of the invention is an eye ointments. A most preferred eye ointment has the following composition:

| | |
|---|---|
| 1. Tacrolimus: | 0.02–0.2 gram; |
| 2. Anhydrous lanolin: | 8–15 gram; |
| 3. Liquid paraffin: | 2–10 gram; |
| 4. Yellow vaseline: | 75–79 gram; and |
| 5. polyoxyethylated castor oil: | 0.8–8 gram |

The eye ointments of the invention may be prepared according to procedures known and used by those skilled in the art.

Another preferred embodiment of the pharmaceutical composition of the invention is an eye cream. According to a particularly preferred embodiment, the eye cream of the invention uses an oil-in-water emulsion as the medicament adjuvant. The eye cream of the invention may be prepared by procedures commonly used in the art.

The present invention further relates to methods for treating immune related ocular diseases, particularly the diseases of the anterior segment of the eye and the eye surface. According to the present invention, pharmaceutical compositions of the present invention comprising tacrolimus are applied topically and locally to the eye.

In rabbits, the methods of the instant invention achieves effective ocular penetration and regardless whether the composition is in the form of eye drops, ointments, or creams, the concentration of the active ingredient reaches therapeutically effective levels, in the target eye tissues, including aqueous humor, cornea, and conjunctiva.

In rats, ocular surface administrations of corticosteroid, tacrolimus, and CsA all show clear inhibition of immune rejection to allotypic transplantation of cornea. The therapeutic action of tacrolimus on cornea transplantation, however, can be elaborated via local immune regulation, thereby resulting in reduced side-effects and lowered cost Clinical tests further demonstrate that the administration of tacrolimus has improved therapeutic effects on the diseases over other immunosuppressants.

The following examples further illustrate the compositions and methods of the instant invention.

PREPARATION EXAMPLE 1

Eye Drops of Tacrolimus with a Concentration of 0.05

| Composition: | |
|---|---|
| 1. Hydroxypropyl methylcellulose: | 0.3 gram |
| 2. Sodium chloride: | 0.75 gram |
| 3. Thimerosal: | 0.002 gram |
| 4. Tacrolimus (FK506): | 0.05 gram |
| 5. HCO60: | 1 gram |
| 6. Water for injection: | add to 100 ml |

The preparation procedure is as discussed above.

Preparation Example 2

Eye Drops of Tacrolimus with a Concentration of 0. 1%

| Composition: | |
|---|---|
| 1. Sodium hyaluronide: | 0.3 gram |
| 2. Sodium chloride: | 1.5 gram |
| 3. Bromogeramine: | 0.01 gram |
| 4. Tacrolimus (FK506): | 0.1 gram |
| 5. HCO60: | 4 gram |
| 6. Water for injection: | add to 100 ml |

The production procedure is the same as above.

Preparation Example 3

Eye Drops of Tacrolimus with a Concentration of 0.2%

| Composition: | |
|---|---|
| 1. Polyvinyl pyrrolidone: | 0.2 gram |
| 2. Ethyl nipagin: | 0.0.5 gram |
| 3. Tacrolimus (FK506): | 0.2 gram |
| 4. HCO60: | 4 gram |
| 5. Water for injection: | add to 100 ml |

The production procedure is the same as above.

Preparation Example 4

Eye Ointment of Tacrolimus with a Concentration of 0.02%

| Composition: | |
|---|---|
| 1. Tacrolimus (FK506): | 0.02 gram |
| 2. Anhydrous lanolin: | 8 gram |
| 3. Liquid paraffin: | 2 gram |
| 4. Yellow vaseline: | 75 gram |
| 5. HCO60: | 2 gram |

Eye ointment preparation is as follows: an appropriate amount of cool aseptic liquid paraffin is added into tacrolimus, grounded into fine cream, filtered with a size 6 sieve; then aseptic and filtered mixture of lanolin and yellow vaseline is gradually added and mixed thoroughly.

Preparation Example 5

Eye Ointment of Tacrolimus with a Concentration of 0.2%

| Composition: | |
|---|---|
| 1. Tacrolimus (FK506): | 0.2 gram |
| 2. Anhydrous lanolin: | 15 gram |
| 3. Liquid paraffin: | 10 gram |
| 4. Yellow vaseline: | 85 gram |
| 5. HCO60: | 0.8 gram |

The preparation procedure is the same as example 4.

EXAMPLE 1

Ocular Pharmacokinetics of the Pharmaceutical Composition of the Invention

Experimental Design: Sixty-two healthy New Zealand white rabbits with body weight ranging from 2.8–3.2 kg were used. Prior to treatment, the animals were examined to ensure that there is no ocular disease.

For each of four eye drop preparations, with different tacrolimus concentrations, four animals were observed for ocular toxicity, side-effects and blood absorption (16 animals total).

For each of the four eye drop preparations, four more animals were used to measure the concentration of tacrolimus in in aqueous humor, conjunctiva, cornea, and iris. For each animal, one eye was treated with the respective eye drop, and the other eye was treated with 0.1% hydroxypropyl methylcellulose.

An amount of 20 μl of tacrolimus eye drops were dropped on corneal surface using micropippet, followed by another 20 μl in five minutes. Samples were prepared after rabbits were anaesthetized by muscular injection of ketamine (2-(2-Chlorophenyl)-2-(methylamino)-cyclohexanone) and chlorpromazine.

Sample Collection

Preparation of aqueous humor samples: conjunctival sacs were washed with normal saline in 0.5 hr, 1 hr, 2 hr, 2.5 hr, 3 hr, and 4 hr, respectively, after the last treatment administration. Anterior chambers of eyes were then punctured along corneal limbus with a 1 ml syringe to collect aqueous humor. The samples were kept in a −18° C. freezer.

Preparation of other tissue samples: animals were killed by air embolism 2.5 hr after the last treatment, corneal epithelia were scraped with a blade, conjunctival sacs were washed with normal saline, samples of aqueous humor were collected, water in conjunctival sacs was removed with cotton swabs, parts of bulbar conjunctiva, cornea, and iris were collected by microscissors, then rinsed with normal saline, blotted with filter paper and placed into 1.5 ml tubes and capped. Samples were weighed with an electronic balance as soon as possible, then removed to 8 ml glass test tubes, 5 ml of methylene dichloride were added and the tissues were cut into fine pieces with microscissors. After centrifugation for 10 minutes, 4.5 ml of methylene dichloride at the bottom were transferred to another tube, and blow-dried with chlorine. The tubes were sealed and kept at 4° C.

The same procedures were applied to the control eyes.

Quantification of Tacrolimus

Measurement of aqueous humor: Tacrolimus concentration was measured with a sensitive technique using competitive immunoenzymatic measurement with monoclonal antibody (MAb) against tacrolimus. It was performed using microtiter plates coated with goat-anti-mouse IgG. The microtiter plates was supplied by DiaSorin Inc., 1990 Industrial Blvd., Stillwater, Minn. 55082, and measurement was conducted to the manufacturer's instructions.

Measurement of Tissue Tacrolimus Concentration: Tacrolimus was first extracted from eye tissues with $CH_2Cl_2$, fully mixed by vortexing, and dissolved in rabbit aqueous

Results

Eyes were treated with tacrolimus eye drops in concentrations of 0.05%, 0.1%, 0.2%, (corresponding to Preparation Examples 1, 2, 3, respectively) and 0.4%. treated eye of the test animal was observed for six months with a slit-lamp and compared with the other, untreated eye. On the third day after treatment, the 4 animals in each group were killed 2.5 hr after the last treatment. Blood was collected and tacrolimus was measured. Corneas were collected and observed with both scanning and transmission electron microscope.

Physical Observation of the Eyes: Slight congestion in bulbar conjunctiva was caused by 0.4% tacrolimus eye drops, but the congestion completely disappeared in 3–4 hr. Swollen cornea and reaction of anterior chamber were not seen. No side-effects were observed in eyes treated with the eye drops having lower tacrolimus concentrations.

Electron Microscopy: no abnormal signs were observed in corneal epithelia and endothelium microvilli, organelles, cellular connections, and normal controls. Fibrous septa of stroma were normal.

Whole blood tacrolimus concentration was measured using the Tacrolimus-II Technique of the IMx system from Abbott Laboratories, Inc. (Abbott Park, Ill.). No tacrolimus was measured in the blood 2.5 hr after administration of any of the eye drops tested.

Results of aqueous humor concentration measurement: 0.5 hr, 1.0 hr, 2.0 hr, 2.5 hr, 3.0 hr, and 4.0 hr after administration of eye drops of 0.05% and 0.1% tacrolimus, aqueous humor was extracted and concentrations of FK506 in aqueous humor were dynamically measured. Aqueous humor was only collected in a certain time point in each rabbit. 5 samples were measured in each time point for each concentration of eye drops. The results demonstrated that after administration with example 1, the concentration of the drug reached its peak value in aqueous humor (18.93±6.95 ng/ml) in 1 hr, tacrolimus could not be measured in 4 hr. Peak value was reached in 1–2 hr after administration of example 2, the concentration in aqueous humor was 28.33±1.36 ng/ml in 2 hr and 3.95±0.55 ng/ml in 4 hr.

In addition, concentrations of tacrolimus in aqueous humor were observed 2.5 hr after administration of tacrolimus in examples 1, 2, 3, and 4%, 4 samples were collected for each eye drop, the results were seen in Table-1. The concentrations of tacrolimus in aqueous humor had significant differences after administration of eye drops in examples 1 and 2, there were no significant differences in the extra groups.

TABLE 1

Concentrations of tacrolimus in aqueous humor 2.5 hr after administration of various concentrations of tacrolimus eye drops

| Concentration of eye drops | Concentration in aqueous humor | t-test |
|---|---|---|
| 0.05 (example 1) | 8.35 ± 0.93 | |
| 0.1 (example 2) | 22.3 ± 5.09 | P = 0.009 |
| 0.2 (example 3) | 24.11 ± 5.38 | P = 0.695 |
| 0.4 | 27.85 ± 10.17 | P = 0.443 |

In our studies there were no differences in concentrations of aqueous humor between each tacrolimus group with concentrations of 0.1% (example 2), 0.2% (example 3), and 0.4%. An increase in concentration of drug may increase stimulation to eyes, causing excretion of tears and an increase in topical blood stream, leading a rapid blood absorption and discharge from lacrimal passage. In addition, there was an abundant blood supply in conjunctiva, resulting in a rapid absorption of tacrolimus in conjunctiva, thus a low amount of the drug. The data of our experiments demonstrated that tacrolimus in each example of our innovation could reach its therapeutic concentration in aqueous humor.

B. Experiments of Prevention of Rejection in Rat Cornea Using Tacrolimus, CsA, and Dexamethasone Purpose: therapeutic effects on immune rejection of allotypic cornea transplantation in rat using a combination of various immunosuppressants are demonstrated, and the best therapeutic method for clinical prevention and treatment of transplantation rejection will be chosen through observation of preventive and therapeutic effects of superficial application of various concentrations of tacrolimus eye drops on immune rejection of allotypic cornea transplantation in rat, and a comparison of individually superficial administration of CsA or dexamethasone with a combination of two.

Method: allotypic cornea transplantation was done using Wister rats as donors and SD rats as recipients. They were divided randomly into control group in which only the carrier was used superficially and treatment groups of 0.05% tacrolimus (example 1) which was used on surface, 0.1% tacrolimus (example 2), 0.05% tacrolimus+0.1% dexamethasone, 0.1% dexamethasone, and 2.5% CsA. Clinical manifestations in different groups, detection of cofocus vivimicroscopy, characterizations of pathology and immunohistochemistry were observed in various time. Concentrations of CsA and tacrolimus in whole blood were detected in the eighth week.

Results: all transplanted corneas in control group appeared obvious opacity and phenomenon of immune rejection in new angiopoiesis in the second week and lasted for 3 weeks. Comparing with control group, transplanted corneas in each treatment group did not show clear rejection and there was a statistically significant difference (p<0.05) between the two groups. Among the treatment groups, transplanted corneas in group of 0.05% tacrolimus+0.1% dexamethasone had better transparency and showed significant differences (P<0.05) in statistics comparing with the other groups except the group of 0.1% dexamethasone. Comparing with the other treatment group, the group containing dexamethasone showed in early phase statistically significant effects on a decrease in swelling and new angiopoiesis of transplanted corneas, while there were no statistical differences among the extra groups. Obvious new angiopoiesis and monocytes infiltration were found in corneal matrix of the control group detected by cofocus microscopy and pathology 15 days after operation, monocytes clearly distributed around and within new angiopoiesis. Matrix swelling was the main sign in the treated groups. Over $\frac{2}{3}$ various immune cells and factors (except B cells) were found decreased in each treated group by immunohistochemistry 15 days after operation, of which the group of 0.05% tacrolimus+0.1% dexamethasone had the best inhibiting effect on cell infiltration. Detection of pathology showed fibrosis of corneal matrix in all treated groups 8 weeks after operation. The average concentration of CsA in rat whole blood was 646.27ng/ml±296.51 in the $8^{th}$ week after operation, and the control group without treatment of CsA eye drops was 0. The average concentration in whole blood was 5.53 ng/ml±3.67 in the group treated with 0.01% tacrolimus (example 2) while the concentrations in the group treated with 0.05% tacrolimus (example 1) and in the control group treated without taccrolimus were 0.

Conclusion: In our animal models superficial administration of corticosteroid, Tecolimus, and CsA showed clearly therapeutic effects on immune rejection in allotypic cornea transplantation. However, it could not completely eliminate immune rejection. Corticosteroid had a strong inhibition effect on inflammation in early phase, and was of the characterizations of causing light swelling and recovering transparency in early transplanted corneas after transplantation. Tacrolimus and CsA had worse therapeutic effects on swelling of transplanted corneas in early phase. All drugs had inhibition effect on new angiopoiesis after cornea transplantation, of which corticosteroid having the strongest effect followed by tacrolimus and CsA. The therapeutic effect of tacrolimus on rejection in corneal transplantation could be realized by topical immune regulation. A combination with corticosteroid clearly enhanced the effect of tarcolimus on topical suppression of immune rejection. In our animal models the effect of immune suppression of superficial administration of CsA could be obtained through systemic absorption of the drug. Further experiments are needed to determine whether it has effect on topical immune regulation. A combined early superficial administration of tacrolimus and corticosteroid may be an ideal therapeutic modality to prevent rejection of corneal transplantation in high risky population. To prevent the side effects of corticosteroid in late phase surface administration of tacrolimus along could be applied after ocular inflammation was stabilized or corneal stitches were removed.

C. Exploring Studies of Clinical Feasibility and Availability of Suppression Effects of FK-506 on Immune Rejection of High Risky Cornea Transplantation Method A prospective evaluation study was applied. 56 high risky patients (56 eyes) who need operation for cornea transplantation were randomly divided into treatment group and control group, each having half patients. Treatment group was topically given 0.5 mg/ml of FK-506 eye drops (example 1), while control group was given 1% CsA eye drops. Average time for follow-up survey was 5½ months. The main criteria for clinical valuation include visual function, lasting time for transparency, new angiopoiesis, swelling, opaque degree of transplanted corneas after operation.

Results

The ratios of rejection to transplanted corneas in treatment and control groups during follow-up survey were 60.8% and 89.3% (u=2.468, p<0.05), respectively. The difference was significant.

Conclusion

Topical administration of FK-506 can effectively inhibit the occurrence of immune rejection of high risky cornea transplantation.

Materials and Methods (A) Case Selection 56 high risky patients (56 eyes) who need operation for cornea transplantation were chosen in this study with 32 eyes from male and 24 from female, average age was 31 (19–66). Of which 27 eyes were carried for full cornea transplantation, 14 for full cornea transplantation with scleral ring, 10 eyes with angiopoiesis cornea were used for cornea transplantation, and 10 for multiple transplantations. Blindness was caused by pyogenic infection of eyes (30 eyes), severe chemical injury (18 eyes), and thermal burn (8 eyes). The aforementioned cases were randomly divided into groups treated with FK-506 or CsA, each having 28 patients (28 eyes).

(B) Medicines

Example 1 was used in the group treated with tacrolimus eye drops.

The control medicine CsA was a product of Swiss Sandoz pharmaceuticals which was diluted to 1% eye drops with oleum ricini. Corticosteroid eye drops was Dianbishu ??? eye drops produced by American Ai4er2kang1 Corporation. ????

(C) Methods of Administration

The above cases were randomly divided into treatment group and control group with each having 28 eyes. The treatment group was given 0.05% (per 100 ml) FK-506 (example 1) and TOBRA DEX® eye drops (Alcon, Inc.) (four times a day, one drop a time), while the control group was given 1% CsA and TOBRA DEX® eye drops (four times a day, one drop a time). Medicines were given 3 days after surgery, continuing 3–9 months, follow-up survey was 5½ months.

(D) Observation Criteria

Observation was done twice a week within 1–3 months after medication, then once a week after 3 months. The items for observation were vision and transplanted corneas (including three criteria: new angiopoiesis, swelling, opacity of transplanted corneas). The scores for each criterion are as follows: new angiopoiesis has grades 0–3, grade 0 indicates no new angiopoiesis (0 score), grade 1 a few new angiopoiesis focusing on transplanted corneas and starting penetration the edges of transplantation (1 score), grade 2 a few new angiopoiesis focusing on center of the transplanted corneas (2 scores), grade 3 a great numbers of new angiopoiesis fully covering the whole transplanted corneas (3 scores). The swelling contains grades 0–3, grade 0 means no swelling (0 score), grade 1 light swelling (1 score), grade 2 medium swelling (2 scores), grade 3 severe swelling (3 scores). The opacity has grades 0–3, grade 0 shows no opacity (0 score), grade 1 light opacity with clear iris stripes (1 score), grade 2 medium opacity and iris still can be seen (2 scores), grade 3 severe opacity and iris and pupil can not be seen (3 scores). Rejection index (RI) is a sum of the previous 3 criteria. When RI=5 scores it is considered rejection. The study would not cover the following conditions: epithelium had reaction of rejection, complication happened during operation, and swelling and dissolution of transplanted corneas occurred after operation due to a functional failure of implanted cornea endothelia, lesion fissure, secondary glaucoma, infection of transplantation.

(E) Results and Statistics

All operations on patients in the study were done by professors in the Department of Corneal Diseases under the unique standard. Donor corneas were all freshly obtained from adults. Specific people were assigned for follow-up survey after surgery. All data were inputted to computer, and t-test, u-test, and analysis of variance were carried on.

Results (A) Vision Post-operation

During the follow-up survey 11 eyes (39.3%) in the group treated with FK-506 had final vision (including those with difficult correction)=0.05, 4 (14.3%) in the group treated with CsA had final vision=0.5, u=2.034, p<0.05, there was a significant difference between the tow eyes with the results of FK-506 group better than that of CsA group.

(B) Rejection Rate of in Cornea Transplantation

The maintenance time for transparency in transplanted corneas after surgery in both FH-506 and CsA groups was 70.4±18.32 days and 41.8±12.75 days (t=6.223, p<0.01), respectively. During the follow-up survey the incidence rates of rejection to the transplantation of tow groups in different phases were shown in Table 2. The results of statistics showed the final incidence rates in two groups were 60.8% (17/28) and 89.3% (25/28), u 2.468 and p<0.05. Starting from the third month after operation the incidence of rejection in FK-506 group was clearly less than that in the CsA group in the same phase, and the clinical effects of FK-506 on immune suppression were much better than CsA.

(C) Other Parameters

During observation the indices of new angiopoiesis, swelling, opaque, and RI values of cornea transplantation in FK-506 and CsA groups were shown in Table 3. The results showed that during the follow-up survey the above four criteria in FK-506 group were much better than CsA group, there was a significant difference between the tow groups. In the aforementioned four parameters the new angiopoiesis had a rapidest change. Changes of four parameters started to show difference 3–4 weeks after operation, while changes in two groups appeared clear difference about three months after surgery.

(D) Adverse Reactions

All patients in FK-506 group had a better tolerance to FK-506. No patients appeared adverse reactions such as twinges, itches, toxic reactions on cornea epithelia. 70% of patients in CsA group showed mild twinges.

In order to effectively solve problems concerning topical administration of FK-506 for eyes we chose high risky cornea transplantations as objects for clinical study. Based on study of pharmacodynamics, test of drug resistance, and pharmacokinetics, a full inquire was performed into the dosage forms, concentrations, clinical titters, and adverse reactions of FK-506 eye drops.

Topical administration of FK-506 eye drops could effectively suppress immune rejection after operation of cornea transplantation with high risky. The results of our study showed that topical administration of FK-506 could extend the transparency and survival time of transplanted corneas in the treatment group, and have much better effective vision and other parameters of rejection than the control group after cornea transplantation with high risky, and especially in medium and late phases after transplantation, its effects on suppressing new angiopoiesis, reducing the incidence rate of swelling and opacity of the transplantation were better than CsA. It provided a therapeutic modality with high clinical value to patients suffering from double blindness and corneal blindness in an adverse condition for their surgery of cornea transplantation. During the studies we could not find any toxic and site effects after topical administration of FK-506 eye drops. Its safety also provided an important prerequisite for widely clinical application.

In addition, we found in our studies that topical administration of tacrolimus also had excellent clinical effects on re-construction of ocular surface and treatment of obstinate and immune corneal diseases (for example erodent corneal ulcer and Wegener's granuloma). In particular, the topical administration of tacrolimus had significant therapeutic effects on Type I and IV hypersensitive reactions. We observed 17 cases of conjunctive inflammation that were non-responsive to CsA treatment, but were successfully controlled by topical administration of tacrolimus. We also observed 64 cases of cornea transplantation, most of which showed significantly reduced rejection reaction when treated with topical tacrolimus. Similarly, of the 26 cases of recurring erosive corneal ulcer, in a period of five months to two years, only three cases had recurrence after topical treatment with tacrolimus.

Topical administration of tacrolimus, however, had some, but not complete therapeutic effect on Types II and III hypersensitive reactions (e.g. Steven Johnson Syndrome.)

All examples of our innovation showed similar outcomes as the example 1.

The innovation was beyond the aforementioned examples.

What is claimed is:

1. A pharmaceutical composition for the treatment of immune-related diseases of ocular surface and the anterior segment of the eye, said composition comprising tacrolimus as an immunosuppressant and polyoxyethylated castor oil in a pharmaceutically acceptable topical formulation, wherein the tacrolimus has a concentration of not more than 2%.

2. The pharmaceutical composition of claim 1, wherein the topical formulation is eye-drop.

3. The pharmaceutical composition of claim 1, wherein the topical formulation is an ointment.

4. The pharmaceutical composition of claim 2, wherein the eye-drop consists essentially of about 0.02–0.2% (g/ml) Tacrolimus, not more than about 1.5% (g/ml) NaCl, and a suitable amount of an antibiotic, in water, wherein the viscosity of the composition is adjusted to 40–50 cP.

5. The pharmaceutical composition of claim 3, wherein the tacrolimus concentration is 0.02–0.2% (g/ml) and the polyoxyethylated castor oil concentration is 0.8–8% (g/ml); and wherein the ointment further comprises 8–15% (g/ml) Anhydrous lanolin; 2–10% (g/ml) Liquid paraffin; and 75–79% (g/ml) Yellow Vaseline.

6. A method for the treatment of immune-response related ocular diseases of the anterior segment of the eye and the eye surface, said method comprising topically administering to a patient in need thereof the pharmaceutical composition of claim 1.

7. The method of claim 6, further comprising administering to the patient a second immunosuppressant.

8. The pharmaceutical composition of claim 1, wherein the tacrolimus has a concentration of not more than 1%.

9. The pharmaceutical composition of claim 1, wherein the tacrolimus has a concentration of not more than 0.05%.

10. The pharmaceutical composition of claim 1, wherein the tacrolimus has a concentration of not more than 0.02%.

* * * * *